United States Patent [19]
Polito et al.

[11] 4,347,058
[45] * Aug. 31, 1982

[54] THYROID POLARIZATION FLUOROIMMUNOASSAY

[75] Inventors: Alan J. Polito, Irvine; Kurtis R. Bray, Garden Grove, both of Calif.

[73] Assignee: Beckman Instruments, Inc., Fullerton, Calif.

[*] Notice: The portion of the term of this patent subsequent to Aug. 31, 1999, has been disclaimed.

[21] Appl. No.: 187,238

[22] Filed: Sep. 15, 1980

[51] Int. Cl.³ .................. G01N 33/52; G01N 33/54; G01N 33/78
[52] U.S. Cl. .................. 23/230 B; 23/923; 424/1.5; 435/7; 435/8
[58] Field of Search .................. 23/230 B; 435/7, 8; 424/1, 1.5, 8

[56] References Cited

U.S. PATENT DOCUMENTS

| | | | |
|---|---|---|---|
| 3,776,698 | 12/1973 | Eisentraut | 23/230 B |
| 3,911,096 | 10/1975 | Chopra | 424/1 |
| 3,941,564 | 3/1976 | Fader et al. | 23/230 B |
| 4,272,505 | 6/1981 | Smith | 23/230 B |

OTHER PUBLICATIONS

Murphy et al., *J. Clin. Endocrinol.*, 24:187, (1964).
Braverman et al., *J. Clin. Endocrinol.*, 32:497, (1971).
Alexander et al., *Clin. Chem.*, 20:553, (1974).
Seth et al., *Clin. Chem.*, 21:1406, (1975).

*Primary Examiner*—Michael S. Marcus
*Attorney, Agent, or Firm*—R. J. Steinmeyer; J. E. Vanderburgh; Robert S. Frieman

[57] ABSTRACT

A polarization fluoroimmunoassay for $T_3$ or $T_4$ thyroid hormones where a serum sample is assayed by contacting the sample with a base to denature the thyroxine binding globulins and thereby form a solution, incubating the solution, contacting the solution with a separating agent and separating bound thyroid hormone from the serum, contacting the separating agent with bound thyroid hormone with an antibody against the thyroid hormone, incubating the separating agent-antibody combination, separating free antibody and thyroid hormone bound antibody from the separating agent, contacting the free antibody with fluorescent labelled thyroid hormone and measuring the fluorescence polarization as an indication of the thyroid hormone in the sample.

11 Claims, 2 Drawing Figures

THYROID POLARIZATION FLUOROIMMUNOASSAY

BACKGROUND OF THE INVENTION

1. Field of the Invention

This invention relates to a thyroid immunoassay and, in particular, to a thyroxine ($T_4$) and triiodothyronine ($T_3$) polarization fluoroimmunoassay.

2. Description of the Prior Art

The assessment of thyroid status in vitro requires the measurement of circulating thyroid hormone levels, notably, thyroxine ($T_4$) and triiodothyronine ($T_3$), which previously was accomplished by methodologies such as protein bound iodine. With the advent of competitive protein binding (CPB) assays, the method of Murphy et al. (1) became in vogue for the estimation of $T_4$ in serum. In the Murphy et al. (1) methodology, $T_4$ is extracted from serum with ethanol or a mixture of ethanol and butanol before analysis via a CPB assay employing thyroxine binding globulin (TBG) as a binder. In order to alleviate the extraction and evaporation steps, Braverman et al. (2) absorbed serum $T_4$ supplemented with radiolabeled hormone onto a small bead-formed dextran gel (sold under the trademark Sephadex) column at pH 12-13. In the alkaline media $T_4$ is released from serum proteins and adsorbed onto the gel. Because the serum components are not retained by the column, a CPB analysis can be performed on the bead-formed dextran gel column using a fixed amount of TBG. The column also serves to separate free and TBG bound $T_4$. Although the column-CPB procedure eliminated the cumbersome extraction and separation steps, a major disadvantage remained in that new columns had to be prepared or purchased for each new test. Finally, Alexendar et al. (3) eliminated this problem by regenerating the columns after each cycle with excess TBG.

Presently, radioimmunoassay (RIA) is the method of choice for the determination of serum $T_4$. The reason for this is that RIA is simpler, quicker, and more specific than the corresponding CPB assays (4, 5). However, a RIA determination in unextracted serum requires the addition of agents to the reaction mixture to prevent the binding of $T_4$ by endogenous serum proteins. Although salicylates (6) and thiomersal (7) have been employed, the most effective reagent has been 8-anilino-1-naphthalene sulfonic acid (ANS) (4). In addition to the direct RIA approach, the beforementioned column methodology has also been applied to give a RIA for serum $T_4$ (8).

Sterling et al. made the interesting observation that thyrotoxicosis may be due to an elevated serum $T_3$ concentration associated with a normal serum $T_4$ level and that a eumetabolic state could be maintained with a low $T_4$ if the serum $T_3$ concentration was within normal limits (9). Although the serum concentration of $T_3$ is only 1-2% of $T_4$, its vital role in thyroid physiology is now generally accepted. Serum $T_3$ concentrations either by saturation analysis after paper chromatography (10) or by gas chromatography (11) are inaccurate, primarily because $T_4$ is deionated to $T_3$ during these procedures. $T_3$ analysis by direct RIA of serum requires (as in the case of direct RIA for $T_4$) the addition of a blocking agent, usually ANS, that prevents binding by endogenous serum proteins (12, 13). Finally, in a similar fashion to the column approach to $T_4$, an RIA methodology has also been described for serum $T_3$ which employs small, reusable bead-formed dextran gel columns (14).

Both an homogenous enzyme immunoassay (EMIT) as well as a more conventional enzyme linked immunoabsorbent assay (ELISA) have been employed for the measurement of serum $T_4$ (15, 16). Although Smith (17) described the preparation of a fluorescent derivative of $T_4$ whose fluorescence is enhanced when bound by anti-$T_4$ serum, this principle cannot be directly applied for the measurement of serum $T_4$ concentration due to the appreciable and variable levels of intrinsic serum fluorescence. A more conventional approach to a fluorometric immunoassay (FIA) for both $T_4$ and $T_3$ based on the separation of free and antibody-bound fractions of labeled ligand, in direct analogy to RIA has been reported by Curry et al. (18). The use of a heterogeneous assay removed most of the serum sample components that might interfer with the measurement of fluorescence from the antibody-bound tracer.

Recently, Schroeder et al. (19) developed an immunoassay for serum $T_4$ that was monitored by chemiluminescence. In this heterogeneous immunoassay, columns absorbed both sample $T_4$ and the $T_4$-chemiluminescent labeled conjugate, while serum components and potential interferents were washed through the column with buffer. After the addition of antibody and an incubation period, the antibody bound $T_4$ was eluted and the labeled hormone detected by a $H_2O_2$-microperoxidase chemiluminescence assay.

Although the basis for fluorescence polarization immunoassay has been described and demonstrated (20), to date other than for the fluorescence polarization assays of gentamicin (21) and dilantin (22), this methodology has not been applied in practical assays of proven clinical utility. For example, in the case of enhancement fluoroimmunoassays (17), it is reported that the variable levels of intrinsic serum fluorescence present an obstacle to the assay of patient sera samples.

BIBLIOGRAPHY

1. Murphy et al., *J. Clin. Endocrinol.*, 24:187 (1964).
2. Braverman et al., *J. Clin. Endocrinol.*, 32;497 (1971).
3. Alexander et al., *Clin. Chem.*, 20:553 (1974).
4. Chopra, *J. Clin. Endocrinol. Metab.*, 34:938 (1972).
5. Ratcliffe et al., *Clin. Endocrinol.* 3:481 (1974).
6. Larsen et al., *J. Clin. Endocrinol. Metab.*, 37:177 (1973).
7. Seth et al., *Clin. Chem.*, 21:1406 (1975).
8. Bartels et al., *Clin. Chim. Acta*, 81:63 (1977).
9. Sterling et al., *J. Clin. Invest.*, 48:1150 (1969).
10. Nauman et al., *J. Clin. Invest.*, 46:1346 (1967).
11. Larsen, *Metabolism*, 20:609 (1971).
12. Malkus et al., *Clin. Chim. Acta*, 51:191 (1974).
13. Chopra et al., *J. Lab. Clin. Med.*, 80:729 (1972).
14. Alexander et al., *Clin. Chem.* 20:1353 (1974).
15. Ullman et al., *Clin. Chem.*, 21:1011 (1975) Abstract.
16. Schall et al., *Clin. Chem.*, 24:1801 (1978).
17. Smith, *F.E.B.S. Let.*, 77:25 (1977).
18. Curry et al., *Clin. Chem.*, 25:1591 (1979).
19. Schroeder et al., *J. of Immunol. Meth.*, 25:275 (1979).
20. Dandliker et al., *Immunochem.* 7:799 (1970).
21. Watson et al., *Clin. Chim. Acta*, 73:51 (1976).
22. McGregor et al., *Clin. Chim. Acta*, 83:161 (1978).

SUMMARY OF THE INVENTION

In accordance with the present invention an improved test for the measurement of circulating thyroid hormone levels, notably, thyroxine ($T_4$) and triiodothyronine ($T_3$), is provided which contains the advantages present in the radioassay technique but which overcomes the problems inherent therein. The test of the instant invention is a polarization fluoroimmunoassay for a thyroid hormone selected from a group consisting of $(T_3)_x$ and $(T_4)_{1-x}$, wherein x is zero or 1. More particularly, the protocol of the thyroid hormone polarization fluoroimmunoassay of the instant invention comprises:

(a) contacting a sample to be assayed with an amount of a suitable base sufficient to denature thyroxine binding globulins present in the sample to thereby form a solution;

(b) incubating the solution;

(c) contacting an aliquot of the solution with a separating agent;

(d) separating thyroid hormone bound to separating agent from serum and thereby simultaneously removing non-specific serum effects as well as background fluorescence;

(e) contacting the thyroid hormone bound to separating agent with an antibody against the thyroid hormone, the antibody having a higher avidity for the thyroid hormone than the avidity of the separating agent for the thyroid hormone;

(f) incubating the separating agent-antibody combination;

(g) separating free antibody and thyroid hormone bound antibody from the separating agent;

(h) contacting the free antibody with fluorescent labeled thyroid hormone; and (i) fluorometrically measuring the fluorescence polarization in the mixture of step (h). The value obtained by the fluorometric measurement of step (i) is directly proportional to the level of the thyroid hormone in the sample being assayed.

DESCRIPTION OF THE PREFERRED EMBODIMENTS

Figure 1:
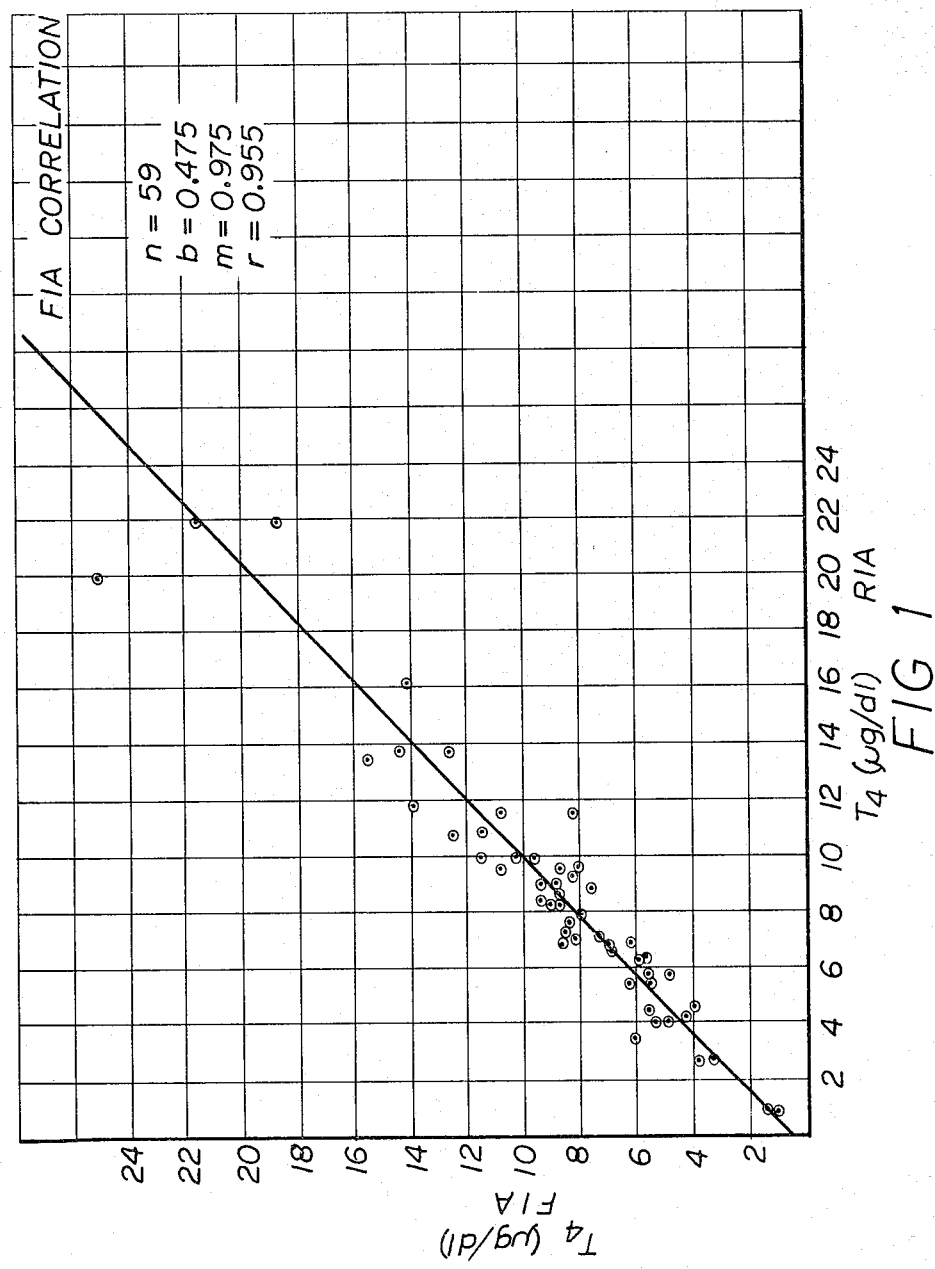
FIG. 1 is a correlation analysis of a radioimmunoassay $T_4$ procedure vs. a polarization fluoroimmunoassay $T_4$ procedure within the scope of this invention.

Samples which can be assayed by the instant invention for a thyroid hormone selected from a group consisting of $(T_3)_x$ and $(T_4)_{1-x}$, wherein x is zero or 1, include biological fluids having an unknown $T_3$ and/or $T_4$ value (e.g., a patient's sample) or biological fluid having a known $T_3$ and/or $T_4$ value (e.g., a standard). Typical biological fluids include, but are not limited to, plasma and serum. Serum is the preferred biological fluid employed in the analysis of the instant invention.

Any separating agents whose avidity for the thyroid hormone being assayed is less than the avidity of serum proteins (most notably TBG) for the thyroid hormone being assayed can be used in the instant invention. Typical separating agents include, but are not limited to, bead-formed dextran gel and agarose. Preferably, the separating agent employed in the instant invention is bead-formed dextran gel.

Any antibody having a higher avidity for the thyroid hormone being assayed than the avidity of the particular separating agent for the thyroid hormone being assayed can be used in the instant invention. Typical thyroid hormone antibodies include, but are not limited to, purified sheep, rabbit, and goat IgG fractions containing thyroid hormone antibody.

Any suitable fluorescent label can be used to label the thyroid hormone. Fluorescent labels include, but are not limited to, fluorescein and rhodamine. Fluorescein is the preferred fluorescent label.

The incubation time of step (b) is not critical and can be any convenient time period. Preferably, this incubation step is conducted for about 1 to about 10 minutes, preferably for about 5 minutes.

In addition, the incubation procedure of step (f) is not critical and can also be conducted for any convenient period of time. Preferably, this incubation step is conducted for about 0.25 to about 2 hours. More preferably, this incubation step is conducted for about 1 hour.

The increase in polarization fluorescence caused by contacting the free antibody with the fluorescent labeled thyroid hormone can be measured by any well known fluorometric technique via an end point or kinetic methodology. Preferably, a kinetic fluorometric technique is employed in the assay of this invention.

Preferably, after step (g) the free antibody is contacted with a non-fluorescent surfactant. Non-fluorescent surfactants include, but are not limited to, octylphenoxy polyethoxy ethanol and polyoxyethylene sorbitan monolaurate. Octylphenoxy polyethoxy ethanol is the preferred non-fluorescent surfactant.

The problems of non-specific binding and variable background fluorescence caused by serum are overcome by step (d) of the procedure of the instant invention when the thyroid hormone which is bound to the separating agent is removed from the serum.

The following examples are provided for the purposes of illustration only and are not intended to be limitations on the disclosed invention.

EXAMPLE 1

Synthesis of Fluorescein Labeled $T_4$ ($FT_4$) and $T_3$ ($FT_3$)

To 4 mg of fluorescein isothiocyanate dissolved in 600 μl of dimethyl formamide were added 4 mg of the appropriate thyroid hormone and the mixture was allowed to stir overnight at room temperature. The fluorescein labeled thyroid hormone was isolated by thin-layered chromatography employing chloroform: methanol:water (60:35:5) as the developing solvent in tanks previously lined with Watman No. 1 brand filter paper. In this system $FT_4$ can be obtained from the non-fluorescent layer band of a doublet with an $R_f$ of 0.3 to 0.4. On the other hand, $FT_3$ can be isolated in one well defined band with an $R_f$ of 0.3 to 0.4.

EXAMPLE 2

$T_4$ Polarization Fluoroimmunoassay

A. Assay Protocol

1. Columns were washed with 6.0 ml of deionized water.

2. Columns were washed with 6.0 ml of 0.1 N NaOH.

3. An aliquot (50 μl) of the sample to be assayed (i.e., standard or patient serum) was mixed with 500 μl of 0.1 N NaOH. The resulting solution was allowed to incubate for about five minutes at room temperature. (This step denatured the TBG and simultaneously solubilized the $T_4$).

4. After the conclusion of incubation step 3, 300 μl of the solution formed in step 3 was contacted with a small, bead-formed dextran gel column whereby the $T_4$ present in the sample being assayed became bound to the dextran gel column. Barbital buffer (3.5 ml, pH 8.6, 0.75 M barbital, 0.9% NaCl, 0.2% EDTA) was employed to wash the column. (This washing procedure removed serum protein and, accordingly, variable background serum fluorescence from the column).

5. Next, 300 μl of antisera specific for $T_4$ was added and allowed to react at room temperature for about 15 minutes with the column bound $T_4$. (In the case of a blank assay, the barbital buffer was employed instead of the antisera).

6. All columns were then washed with 1.5 ml of the barbital buffer and the eluents were collected in falcon tubes.

7. To each falcon tube was then added 100 ml of the barbital buffer containing 0.01% v/v octylphenoxy polyethoxy ethanol surfactant.

8. Aliquots (500 μl) from each falcon tube were reacted with fluorescein labeled $T_4$ and the resulting fluorescein polarization of the aliquot was measured.

The data obtained from this example are set forth in Table I together with data obtained from assaying the same samples via a commercial radioimmunoassay (RIA) procedure. The data of Table I are plotted in FIG. 1.

TABLE 1

| $T_4$ FIA vs $T_4$ RIA Correlation Analysis | | |
|---|---|---|
| Sample No. | RIA μg/dl | FIA μg/dl |
| 1 | 22.0 | 18.7 |
| 2 | 16.2 | 14.1 |
| 3 | 9.5 | 8.6 |
| 4 | 13.7 | 12.6 |
| 5 | 3.6 | 5.9 |
| 6 | 9.0 | 8.9 |
| 7 | 4.2 | 5.4 |
| 8 | 4.2 | 5.0 |
| 9 | 4.4 | 5.5 |
| 10 | 2.8 | 3.4 |
| 11 | 1.0 | 1.0 |
| 12 | 2.9 | 3.7 |
| 13 | 10.9 | 11.6 |
| 14 | 8.1 | 8.0 |
| 15 | 6.3 | 5.9 |
| 16 | 5.5 | 5.4 |
| 17 | 7.6 | 7.8 |
| 18 | 7.0 | 8.5 |
| 19 | 13.8 | 14.4 |
| 20 | 11.9 | 13.8 |
| 21 | 9.9 | 11.4 |
| 22 | 4.2 | 4.2 |
| 23 | 22.0 | 21.6 |
| 24 | 7.8 | 7.8 |
| 25 | 5.5 | 5.8 |
| 26 | 6.7 | 7.0 |
| 27 | 6.4 | 5.5 |
| 28 | 11.6 | 8.2 |
| 29 | 8.6 | 8.6 |
| 30 | 12.4 | 10.8 |
| 31 | 9.4 | 8.2 |
| 32 | 8.8 | 8.8 |
| 33 | 6.9 | 6.9 |
| 34 | 7.5 | 8.4 |
| 35 | 8.9 | 9.1 |
| 36 | 4.6 | 4.0 |
| 37 | 9.6 | 8.0 |
| 38 | 5.6 | 5.4 |
| 39 | 9.8 | 9.6 |
| 40 | 7.5 | 8.4 |
| 41 | 7.2 | 7.3 |
| 42 | 9.9 | 10.1 |
| 43 | 20.0 | 25.2 |
| 44 | 1.0 | 1.4 |
| 45 | 8.3 | 8.6 |
| 46 | 7.1 | 8.2 |

TABLE 1-continued

| $T_4$ FIA vs $T_4$ RIA Correlation Analysis | | |
|---|---|---|
| Sample No. | RIA μg/dl | FIA μg/dl |
| 47 | 13.5 | 15.5 |
| 48 | 8.4 | 9.2 |
| 49 | 9.8 | 10.1 |
| 50 | 11.6 | 10.8 |
| 51 | 7.7 | 8.0 |
| 52 | 8.3 | 8.9 |
| 53 | 5.6 | 6.2 |
| 54 | 9.6 | 10.7 |
| 55 | 8.9 | 7.6 |
| 56 | 5.8 | 4.8 |
| 57 | 7.9 | 7.7 |
| 58 | 6.9 | 6.1 |
| 59 | 5.7 | 5.8 |
| $n^1 = 59$ | | |
| $b^2 = 0.475$ | | |
| $m^3 = 0.975$ | | |
| $r^4 = 0.955$ | | |

[1] n = number of samples
[2] b = intercept
[3] m = slope
[4] r = correlation coefficient A statistical analysis of the data obtained via the $T_4$ RIA methodolody with that obtained with a $T_4$ polarization fluoroimmunoassay within the scope of the present invention yields a regression line having the formula $Y = 0.957X + 0.475$ and a correlation coefficient (r) equal to 0.955. The $T_4$ RIA methodolog and the $T_4$ polarization fluoroimmunoassay methodology of the instant invention yield comparable data as shown by the fact that the regression coefficient (slope) equals 0.957, the correlation coefficient equals 0.955, and the intercept equals 0.457 μg/dl, i.e., either method can be used for the quantitative measurement of $T_4$.

EXAMPLE 3

$T_3$ Polarization Fluoroimmunoassay

A. Assay Protocol

1. Columns were washed with 6.0 ml of deionized water.

2. Columns were washed with 6.0 ml of 0.1 N NaOH.

3. An aliquot (300 μl) of the sample to be assayed (i.e., standard or patient serum) was mixed with 300 μl of 0.1 N NaOH. The resulting solution was allowed to incubate for about five minutes at room temperature. (This step denatured the TBG and simultaneously solubilized the $T_3$).

4. After the conclusion of incubation step 3, 400 μl of the solution formed in step 3 was contacted with a small, bead-formed dextran gel column, whereby the $T_3$ present in the sample being assayed became bound to the dextran gel column. A barbital buffer (0.75 M barbital, 0.9% NaCl, 0.2% EDTA, pH 8.6) was employed to wash the column. (This washing procedure removed serum protein and, accordingly, variable background serum fluorescein from the column).

5. Next, 300 μl of antisera specific for $T_3$ was added and allowed to react at room temperature for about 1 hour with the column bound $T_3$. (In the case of a blank assay, the barbital buffer was employed instead of the antisera.)

6. All columns were then washed with 1.5 ml of the barbital buffer and the eluents were collected in falcon tubes.

7. To each falcon tube was then added 100 ml of the barbital buffer containing 0.01% v/v octylphenoxy polyethoxy ethanol surfactant.

8. Aliquots (500 μl) from each falcon tube were reacted with fluorecein labeled $T_3$ and the resulting fluorescein polarization of the aliquot was measured.

Figure 2:
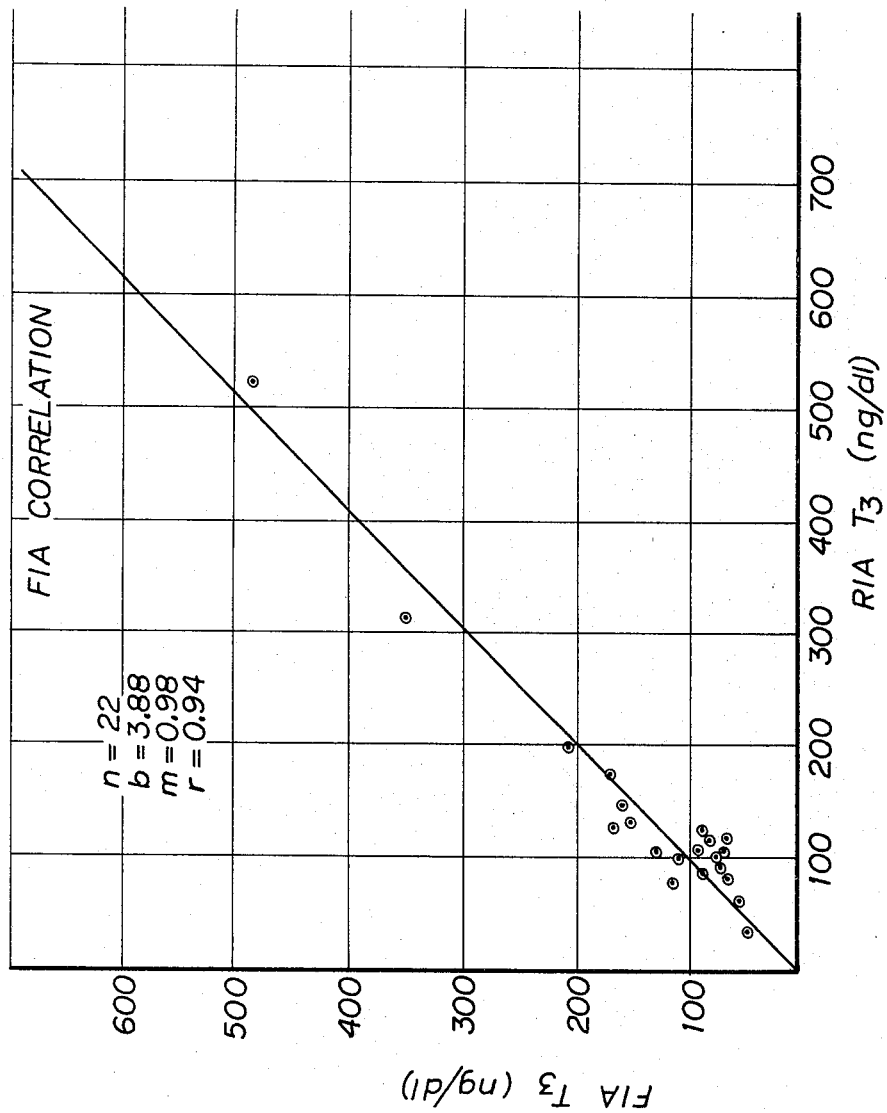
FIG. 2 is a correlation analysis of a radioimmunoassay $T_3$ procedure vs. a polarization fluoroimmunoassay $T_3$ procedure within the scope of this invention.

The data obtained from this example are set forth in Table II together with data obtained from assaying the same samples via a commercial $T_3$ RIA procedure. The data of Table I are plotted in FIG. 2.

TABLE II $T_3$ FIA vs $T_3$ RIA Correlation Analysis

| Sample No. | RIA ng/dl | FIA ng/dl |
|---|---|---|
| 1 | 111 | 92 |
| 1 | 134 | 155 |
| 3 | 149 | 160 |
| 4 | 128 | 87 |
| 5 | 106 | 70 |
| 6 | 96 | 108 |
| 7 | 80 | 117 |
| 8 | 177 | 170 |
| 9 | 315 | 351 |
| 10 | 92 | 71 |
| 11 | 37 | 48 |
| 12 | 202 | 207 |
| 13 | 128 | 168 |
| 14 | 102 | 75 |
| 15 | 89 | 91 |
| 16 | 121 | 84 |
| 17 | 106 | 131 |
| 18 | 141 | 254 |
| 19 | 523 | 487 |
| 20 | 81 | 66 |
| 21 | 120 | 70 |
| 22 | 64 | 54 |

$n^1 = 22$
$b^2 = 3.88$
$m^3 = 0.98$
$r^4 = 0.94$

[1]n = number of samples
[2]b = intercept
[3]m = slope
[4]r = correlation coefficient A statistical analysis of the data obtained via the $T_3$ RIA methodology with that obtained with a $T_3$ polarization fluoroimmunoassay methodology within the scope of the present invention yields a regression line having the formula $Y = 0.98X + 3.88$ and a correlation coefficient (r) equal to 0.94. The $T_3$ RIA metology and the $T_3$ polarization fluoroimmunoassay methodology of the instant invention yield comparable data as shown by the fact that the regression coefficient (slope) equals 0.98, the correlation coefficient equals 0.94, and the intercept equals 3.88 ng/dl, i.e., either method can be used for the quantitative measurement of $T_3$.

EXAMPLE 3

Various $T_4$ Standards and a blank sample were assayed in duplicate by the procedure set forth in Example 1 and the data obtained therefrom is set forth in Table III.

Table III shows that an FIA for $T_4$ within the scope of this invention has a good average coefficient of variation, i.e., less than about 1%. In addition, since the normal $T_4$ value (8 μg/dl) falls approximately at the mid point of the standard curve, i.e., at 59.05% $(B-B_1)/(B_0-B_1)$ this FIA for $T_4$ possesses a good sensitivity.

TABLE III

Within Run Precision FIA for $T_4$

| Standard | $V_v - H_v$ | $\overline{(X)}$ | % CV | $\% \left( \frac{B - B_1}{B_0 - B_1} \right)$ |
|---|---|---|---|---|
| Blank | 185 | 184 | 1.16% | |
| | 182 | | | |
| 0 μg/dl | 981 | 980 | 0.22% | 100.00 |
| | 978 | | | |
| 2 μg/dl | 914 | 912 | 0.31% | 91.46 |
| | 910 | | | |
| 4 μg/dl | 798 | 799 | 0.18% | 77.26 |
| | 800 | | | |
| 8 μg/dl | 644 | 658 | 3.11% | 59.05 |
| | 673 | | | |
| 12 mg/dl | 543 | 547 | 1.03% | 45.60 |
| | 551 | | | |
| 20 μg/dl | 446 | 448 | 0.47% | 33.17 |
| | 449 | | | |
| 32 μg/dl | 391 | 390 | 0.18% | 25.88 |
| | 390 | | 0.83% Avg. | |

EXAMPLE 4

Various $T_3$ Standards and a blank sample were assayed in duplicate by the procedure set forth in Example 2 and the data obtained therefrom is set forth in Table IV.

Table IV shows that an FIA for $T_3$ within the scope of this invention has a good average coefficient of variation, i.e., less than about 1%. In addition, since the high end of the normal range for $T_3$ (200 ng/dl) falls close to the midpoint of the standard curve, i.e., at 64.38% $(B-B_1)/(B_0-B_1)$ this FIA for $T_3$ also possesses a good sensitivity.

TABLE IV

Within Run Precision FIA for $T_3$

| Standard | $V_v - H_v$ | $\overline{(X)}$ | % CV | $\% \left( \frac{B - B_1}{B_0 - B_1} \right)$ |
|---|---|---|---|---|
| Blank | 290 | 290 | 0.24% | |
| | 291 | | | |
| Bo | 912 | 916 | 0.69% | 100.00 |
| | 921 | | | |
| 50 Ng/dl | 821 | 834 | 2.12% | 86.90 |
| | 846 | | | |
| 100 ng/dl | 759 | 772 | 2.38% | 77.00 |
| | 785 | | | |
| 200 ng/dl | 694 | 694 | 0.10% | 64.38 |
| | 693 | | | |
| 300 ng/dl | 621 | 622 | 0.11% | 52.88 |
| | 622 | | | |
| 500 ng/dl | 488 | 492 | 1.29% | 32.27 |
| | 497 | | 0.99% Avg. | |

EXAMPLE 5

Various $T_4$ standards and a blank sample were assayed in duplicate on 8 different occasions via the procedure of Example 1. The results of the data obtained therefrom are set forth in Table V.

EXAMPLE 6

Various $T_3$ standards and a blank sample were assayed on 5 different occasions via the procedure of Example 2. The results of the data obtained therefrom are set forth in Table VI.

TABLE V

Between Run Precision
FIA Assay for Thyroxine $$\% \left( \frac{B - B1}{Bo - B1} \right)$$

| Standard | 1 | 2 | 3 | 4 | 5 | 6 | 7 | 8 | Avg | % CV |
|---|---|---|---|---|---|---|---|---|---|---|
| 2 μg/dl | 90.38 | 91.46 | 87.75 | 92.57 | 88.97 | 87.48 | 89.64 | 89.57 | 89.73 | 1.93 |
| 4 μg/dl | 75.27 | 77.26 | 75.63 | 79.13 | 76.54 | 78.33 | 75.44 | 76.69 | 76.79 | 1.82 |
| 8 μg/dl | 62.09 | 59.05 | 56.39 | 61.72 | 57.68 | 60.16 | 59.47 | 59.21 | 59.47 | 3.20 |
| 12 μg/dl | 47.66 | 45.60 | 47.69 | 52.37 | 49.58 | 51.68 | 48.82 | 47.70 | 48.89 | 4.61 |
| 20 μg/dl | 36.81 | 33.17 | 32.41 | 38.28 | 34.08 | 36.07 | 38.17 | 38.21 | 35.90 | 6.65 |
| 32 μg/dl | 29.12 | 25.88 | 26.09 | 30.60 | 28.49 | 30.28 | 27.66 | 31.17 | 28.66 | 7.01 |
| | | | | | | | | | Avg | 4.20 |

TABLE VI

Between Run Precision
FIA Assay for Triiodothyrone $$\% \left( \frac{B - B1}{Bo - B1} \right)$$

| Standard | 1 | 2 | 3 | 4 | 5 | Avg | % CV |
|---|---|---|---|---|---|---|---|
| 50 ng/dl | 91.75 | 88.91 | 84.55 | 86.04 | 86.90 | 87.63 | 3.19 |
| 100 ng/dl | 79.52 | 78.61 | 73.17 | 75.28 | 77.00 | 76.72 | 3.33 |
| 200 ng/dl | 63.16 | 63.39 | 58.86 | 61.89 | 64.38 | 62.34 | 3.43 |
| 300 ng/dl | 50.07 | 49.76 | 45.53 | 48.80 | 52.88 | 49.31 | 5.45 |
| 500 ng/dl | 29.30 | 28.53 | 25.69 | 30.19 | 32.27 | 29.20 | 8.25 |
| | | | | | | Avg | 4.73 |

Tables V and VI show that an FIA for $T_4$ and an FIA for $T_3$, respectively, within the scope of this invention have a good day to day precision throughout the standard curve, namely, an average day to day CV of 4.20% and 4.73%, respectively.

Based upon this disclosure, many other modifications and ramifications will naturally suggest themselves to those skilled in the art. These are intended to be comprehended as within the scope of this invention.

The embodiments of the invention in which an exclusive property or privilege is claimed are defined as follows:

1. A polarization fluoroimmunoassay for a thyroid hormone selected from a group consisting of $(T_3)_x$ and $(T_4)_{1-x}$, wherein x is 0 or 1 comprising:
   (a) contacting a serum sample to be assayed with an amount of a suitable base sufficient to denature thyroxine binding globulins present in said serum sample to thereby form a solution;
   (b) incubating said solution;
   (c) contacting an aliquot of said solution with a separating agent;
   (d) separating thyroid hormone bound to separating agent from serum and thereby simultaneously removing non-specific serum effects as well as background fluorescence;
   (e) contacting said thyroid hormone bound to separating agent with an antibody against said thyroid hormone, said antibody having a higher affinity for said thyroid hormone than the affinity of said separating agent for said thyroid hormone;
   (f) incubating said separating agent-antibody combination;
   (g) separating free antibody and thyroid hormone bound antibody from said separating agent;
   (h) contacting said free antibody with fluorescent labeled thyroid hormone; and
   (i) fluorometrically measuring the fluorescence polarization in said mixture of step (h); wherein said measurement is directly proportional to the level of said thyroid hormone in the serum sample being assayed.

2. The assay of claim 1 wherein said separating agent is selected from a group consisting of bead-formed dextran gel and agarose.

3. The assay of claim 1 wherein said fluorescent labeled thyroid hormone is selected from a group consisting of fluoroescein labeled thyroid hormone and rhodamine labeled thyroid hormone.

4. The assay of claim 1 wherein after step (g) a non-fluorecent surfactant is contacted with said free antibody.

5. The assay of claim 1 wherein:
   (a) said separating agent is selected from a group consisting of bead-formed dextran gel and agarose;
   (b) said fluorescent labeled thyroid hormone is selected from a group consisting of fluorescein labeled thyroid hormone and rhodamine labeled thyroid hormone; and
   (c) after step (g) said free antibody is contacted with a non-fluorescent surfactant.

6. The assay of claim 5 wherein said separating agent is bead-formed dextran gel.

7. The assay of claim 5 wherein said fluorescent labeled thyroid hormone is fluorescein labeled thyroid hormone.

8. The assay of claim 5 wherein said non-fluorescent surfactant is selected from a group consisting of oxylphenoxy polyethoxy ethanol and polyoxyethylene sorbitan monolaurate.

9. The assay of claim 5 wherein:
   (a) said separating agent is bead-formed dextran gel;
   (b) said fluorescent labeled thyroid hormone is fluorescein labeled thyroid hormone; and
   (c) said non-fluorescent surfactant is selected from a group consisting of oxylphenoxy polyethoxy ethanol and polyoxyethylene sorbitan monolaurate.

10. The assay of claim 9 wherein said non-fluorescent surfactant is octylphenoxy polyethoxy ethanol.

11. The assay of any one of claims 1-10 wherein said fluorometric measurement is a kinetic fluorometric measurement.

* * * * *